United States Patent [19]

Johanson

[11] Patent Number: 4,715,212

[45] Date of Patent: Dec. 29, 1987

[54] BULK SOLIDS PROPERTY TESTER

[75] Inventor: Jerry R. Johanson, San Luis Obispo, Calif.

[73] Assignee: Jenike & Johanson, Inc., North Billerica, Mass.

[21] Appl. No.: 855,311

[22] Filed: Apr. 24, 1986

[51] Int. Cl.[4] .............................................. G01N 3/00
[52] U.S. Cl. ......................................... 73/38; 73/794
[58] Field of Search ................... 73/794, 798, 825, 37, 73/38

[56] References Cited

U.S. PATENT DOCUMENTS

| 2,810,289 | 10/1957 | Button | 73/825 |
| 2,880,609 | 4/1959 | Byrkett et al. | 73/38 |
| 3,035,437 | 5/1962 | Watkins et al. | 73/825 |
| 3,478,572 | 11/1969 | McRae et al. | 73/825 |
| 3,538,758 | 11/1970 | Karper et al. | 73/794 |
| 3,593,573 | 7/1971 | Ely | 73/825 |
| 3,975,950 | 8/1976 | Erdei | 73/825 |
| 4,502,338 | 3/1985 | Smith et al. | 73/825 |

FOREIGN PATENT DOCUMENTS

| 179785 | 12/1962 | Sweden | 73/825 |
| 459708 | 6/1972 | U.S.S.R. | 73/794 |
| 868440 | 10/1981 | U.S.S.R. | 73/794 |
| 1118895 | 10/1984 | U.S.S.R. | 73/825 |

OTHER PUBLICATIONS

Article, *Flow Properties of Bulk Solids* (Jenike, Elsey and Woolley), proceedings of the American Society for Testing Materials, vol. 60, pp. 1168–1181.

Primary Examiner—Michael J. Tokar
Assistant Examiner—Hezron E. Williams
Attorney, Agent, or Firm—Jeremiah Lynch

[57] ABSTRACT

Apparatus and method for testing the internal friction and yield strength properties of bulk solids, for use in the design of material handling equipment. A sample of the solids is confined under controlled pressure in a test cell having an annular wall converging from one end of larger cross section downwardly toward a second end of smaller cross section. The pressure at the one end is varied until the ratio of the two pressures becomes constant. The two resulting pressures are then used together with the separately measured bulk density of the solids and the angle of friction thereof with the wall of the test cell to compute the effective angle of internal friction. By a further step including removal of the pressure applying means at the other end the unconfined yield strength may be determined.

15 Claims, 9 Drawing Figures

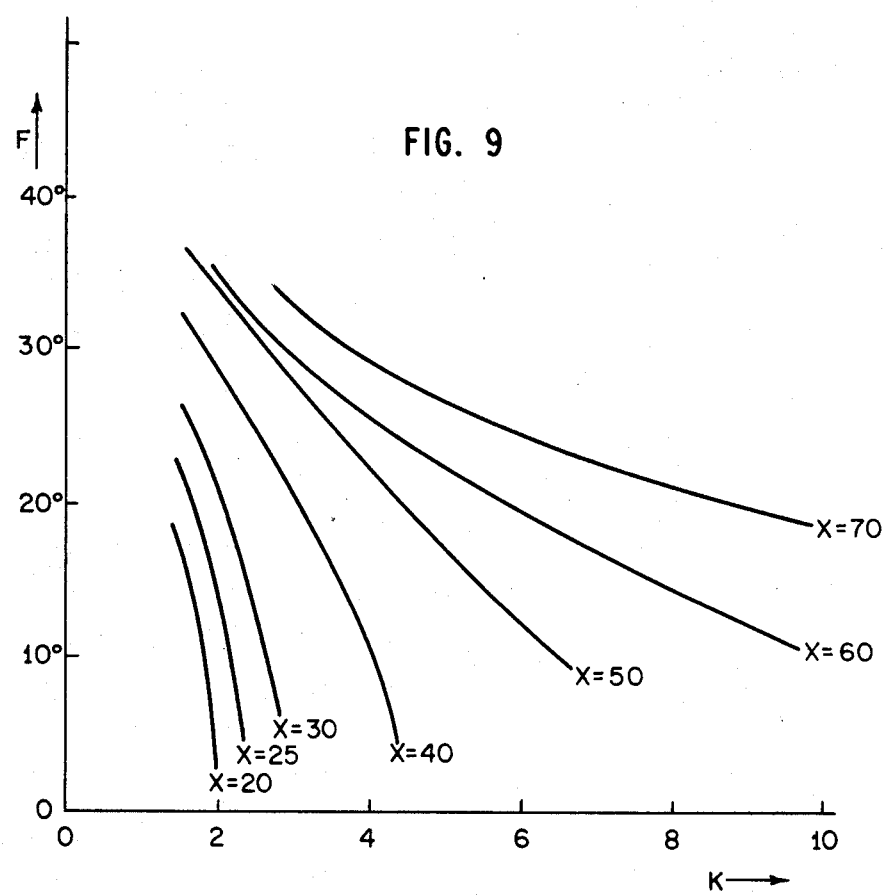

BULK SOLIDS PROPERTY TESTER

SUMMARY OF THE INVENTION

This invention relates generally to methods and apparatus for measuring the properties of bulk solids, such as powders, granular materials and other particulate materials, for the purpose of predicting their flow properties in bins and other material handling equipment. More particularly, the invention relates to methods and apparatus for obtaining the unconfined yield strength "$f_c$", the effective angle of internal friction "x", and the bulk density "D" of particulate or bulk solids. This information, together with the coefficient of friction between the bulk solid and the wall surface of the material handling equipment, separately determined by a conventional test, are used to predict critical arching and ratholing dimensions in bins.

Direct shear testers are known. Descriptions may be found in an article entitled "Flow Properties of Bulk Solids" in *Proceedings of the American Society for Testing Materials*, Vol. 60, pages 1168 to 1181, by Jenike, Elsey and Woolley; and a Bulletin entitled "Storage and Flow of Solids", Bul. No. 123 of the University of Utah Engineering Experiment Station, November 1964, By Jenike.

These references describe a test cell comprising a stationary lower part in which the bulk solid to be tested is placed, and a movable upper part including a cover through which a force load is applied. Prior to conducting the test, the bulk solid is prepared under the same conditions of pressure, temperature, chemical reaction and time as would occur in the material handling equipment. In the test, a vertical force load is applied to the bulk solids through the cover, and a lateral shearing force is applied to cause the material to yield under the forces. Measurements of these forces are taken, and after several samples of the material have been sheared an indirect measure is obtained of the unconfined yield strength $f_c$ and the effective angle of internal friction x. The wide use of the method to date is attributable to the relaibility of the results obtained, and the method has been extended to conditions of high gas pressure and high temperature. However, direct shear testing with such apparatus is time consuming and cumbersome, in that it requires several tests to determine a single value of $f_c$ for a particular level of consolidation of the bulk solids.

A principal object of this invention is to provide a method and apparatus for obtaining by measurement the same properties of bulk solids previously obtained by direct shear testing with the apparatus described in the above references, but utilizing a single test in place of multiple tests, thereby greatly speeding up the testing procedure.

Another object is to perform the test under more uniform stress conditions than those that generally apply in shear cells of the type previously used.

With the foregoing and other objects hereinafter appearing in view, the features of this invention include a test cell for containing the bulk solids, having an annular wall converging downwardly from an upper end of greater cross sectional area to a lower end of lesser cross sectional area, with means for independently applying pressure to the bulk solids at both of said ends and for measuring said pressures.

The test procedure of this invention comprises a number of steps. The material is first compacted to a level simulating the conditions in material handling equipment such as equipment for storing, loading, unloading and process feeding, including simulated conditions as to the level of compaction, temperature, chemical reaction, and gas flow. Thereafter, in successive steps the pressure applying means are operated while observing and recording the top and bottom pressures. After the ratio between these pressures reaches a steady state computations are performed which, with previously measured properties of the bulk solids, will enable a determination of the effective angle of internal friction x.

In a further step, the lower pressure applying means is removed, and the pressure applied by the upper pressure applying means is increased until a failure of the bulk solids is observed. From the top pressure applied at this moment the unconfined yield strength $f_c$ may be determined.

Similar apparatus may also be employed for separately measuring the bulk density of the solids.

DESCRIPTION OF THE DRAWINGS

FIG. 9 is an illustrative graph showing the relationship of the angle of internal friction x to values of the angle of surface friction and K-values computed as hereinafter described.

DETAILED DESCRIPTION

Figure 2:
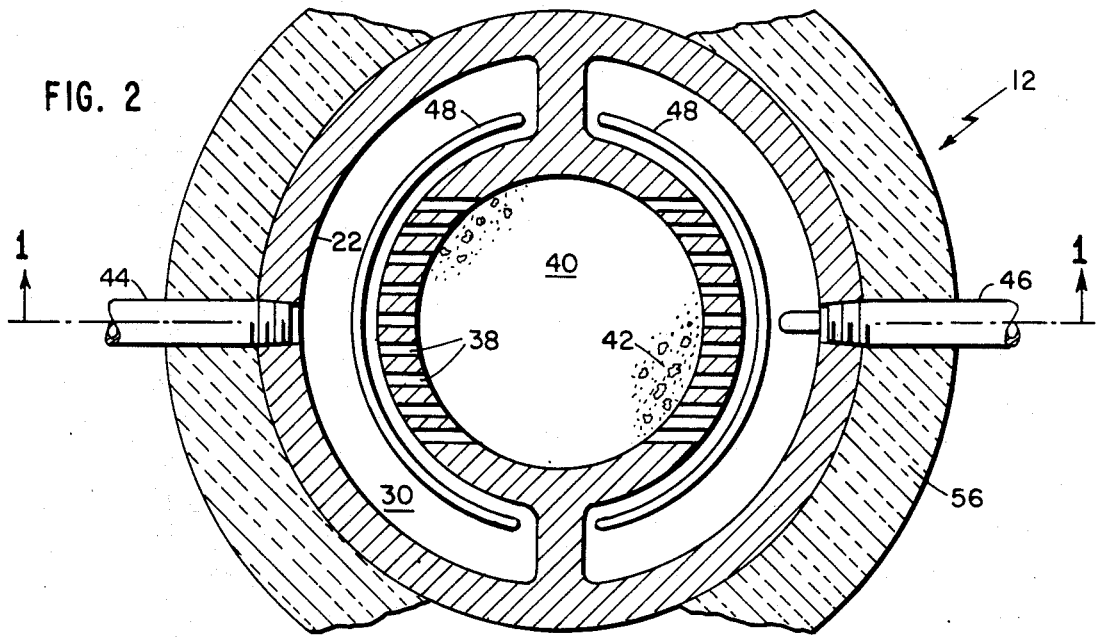
FIG. 2 is a plan view in section taken on line 2—2 of FIG. 1.
Figure 1:
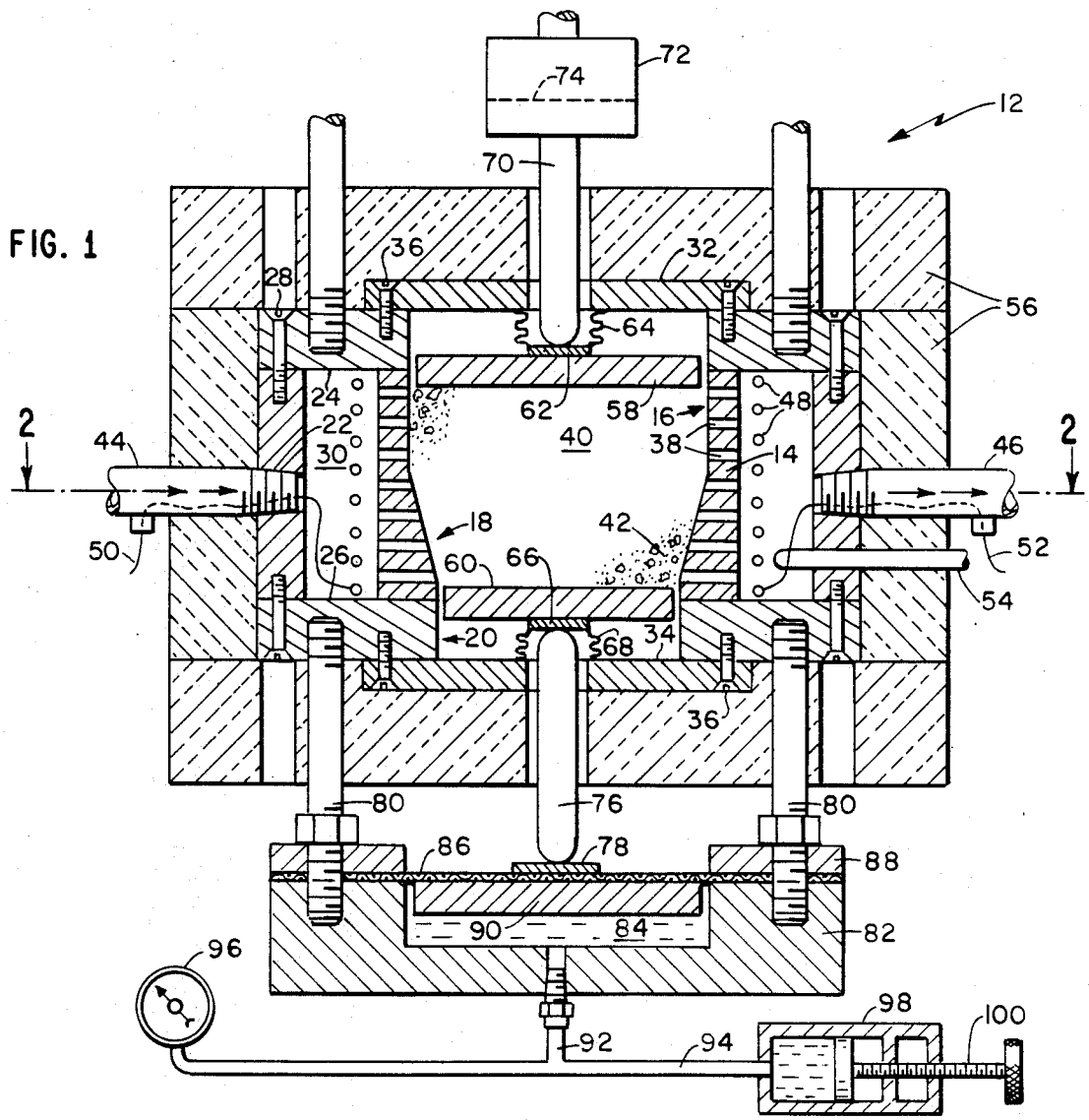
FIG. 1 is an elevation in section of a preferred embodiment of the invention for use under a variety of simulated conditions.

FIGS. 1 and 2 illustrate the preferred embodiment of the invention for obtaining the effective angle of internal friction x and the unconfined yield strength $f_c$ under a wide variety of conditions and states of the bulk solids, simulating the conditions existing in the handling equipment in which the solids are intended to be used. The apparatus, designated generally 12, includes a cell 14 having an upper cylindrical section 16, a conical section 18 and a lower cylindrical section 20. An outer cylindrical wall 22 is secured to upper and lower plates 24 and 26, respectively, by screws 28. These plates support the cell 14 and outer wall 22 in spaced concentric relationship to form an annular space 30. The plate 24 is apertured to form an inner wall surface flush with the cylindrical section 16. Likewise, the plate 26 is apertured to form an inner wall surface flush with the lower cylindrical section 20. The apertures in the plates 24 and 26 are covered by plates 32 and 34, respectively, by screws such as 36.

The cell 14 has a number of radial apertures 38 extending through its wall and forming any desired pattern. These apertures provide communication for liquid or gas between a test chamber 40 occupied by a body of bulk solids 42 under test and the space 30. An inlet duct 44 and an outlet duct 46 provide means for conducting gas or liquid into, through and from the test chamber 40 to simulate the environment to which the bulk solids 42 may be subjected under field flow conditions, including any chemical reactions that may occur.

To obtain the desired temperature of the bulk solids annular or other conveniently shaped heating or cooling elements 48 installed in the annular space 30. When the elements 48 are resistance heating elements, suitable leads 50 and 52 are connected through the ducts 44 and 46 for making external connections to a power source (not shown). To control the temperature at a predetermined value, a thermocouple is mounted within a suitable temperature measurement probe 54 and connected to the power source.

Bodies 56 of heat insulating material are preferably arranged to cover the above-described elements, as shown.

An upper plunger 58 is preferably located within the upper cylindrical section 16 of the test chamber, and similarly, a lower plunger 60 is located within the lower cylindrical section 20. A bearing plate 62 and metallic bellows 64 enclose an upper axial opening into the test cell. The plate 62 is secured to the plunger 58. Similarly, a bearing plate 66 and a metallic bellows 68 enclose a lower axial opening into the cell. The plate 66 is secured to the plunger 60.

Means are provided to apply a measured pressure to the cross sectional area of the bulk solids under test at a first or upper end thereof by means of the plunger 58. Similarly, means are independently provided for applying a measured pressure to the cross sectional area of a second or lower end of the solids by means of the plunger 60. The pressure is applied at the upper end by means of a force rod 70 connected with a suitable force applying means 72 of any desired form, the applied force being measured by a load cell 74 which may be any desired form of force sensor.

The force is applied at the lower end of the test cell by a force rod 76 bearing upon a pressure pad 78. Pressure is applied to the rod 76 by means of a structure supported on studs 80 threaded into the plate 26. The studs support an assembly comprising a housing 82 containing liquid 84 and closed by a diaphragm 86 sealed at its periphery by a closure plate 88. The diaphragm is held between the bearing plate 78 and a plate 90. The liquid 84 communicates through pipes 92 and 94 with a pressure gauge 96 and manually operated pressure-applying means consisting of a cylinder 98 and screw plunger 100.

It will be observed that the test chamber 40 is sealed, whereby fluids can only pass into, through and from the test chamber 40 by way of the ducts 44 and 46. When the test conditions do not require any fluid to be introduced into the test chamber, the ports 38 and ducts are open for the escape of air from the mass of the bulk solids 42 as they are compacted.

Figure 4:
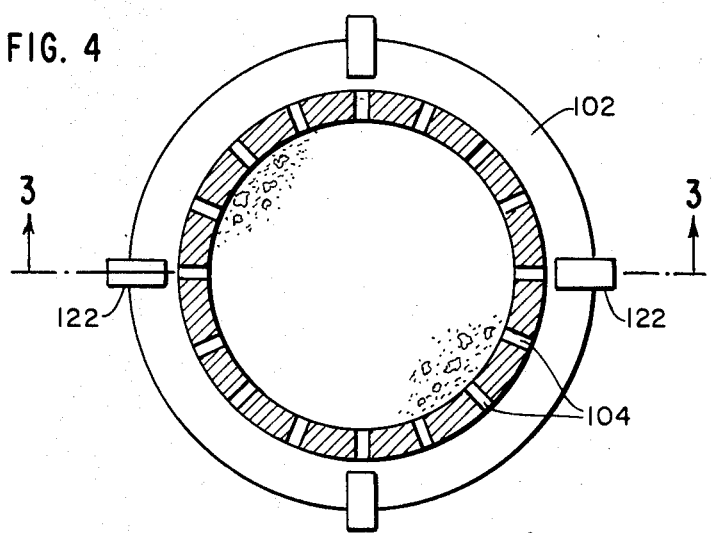
FIG. 4 is a plan view in section taken one line 4—4 of FIG. 3.
Figure 3:
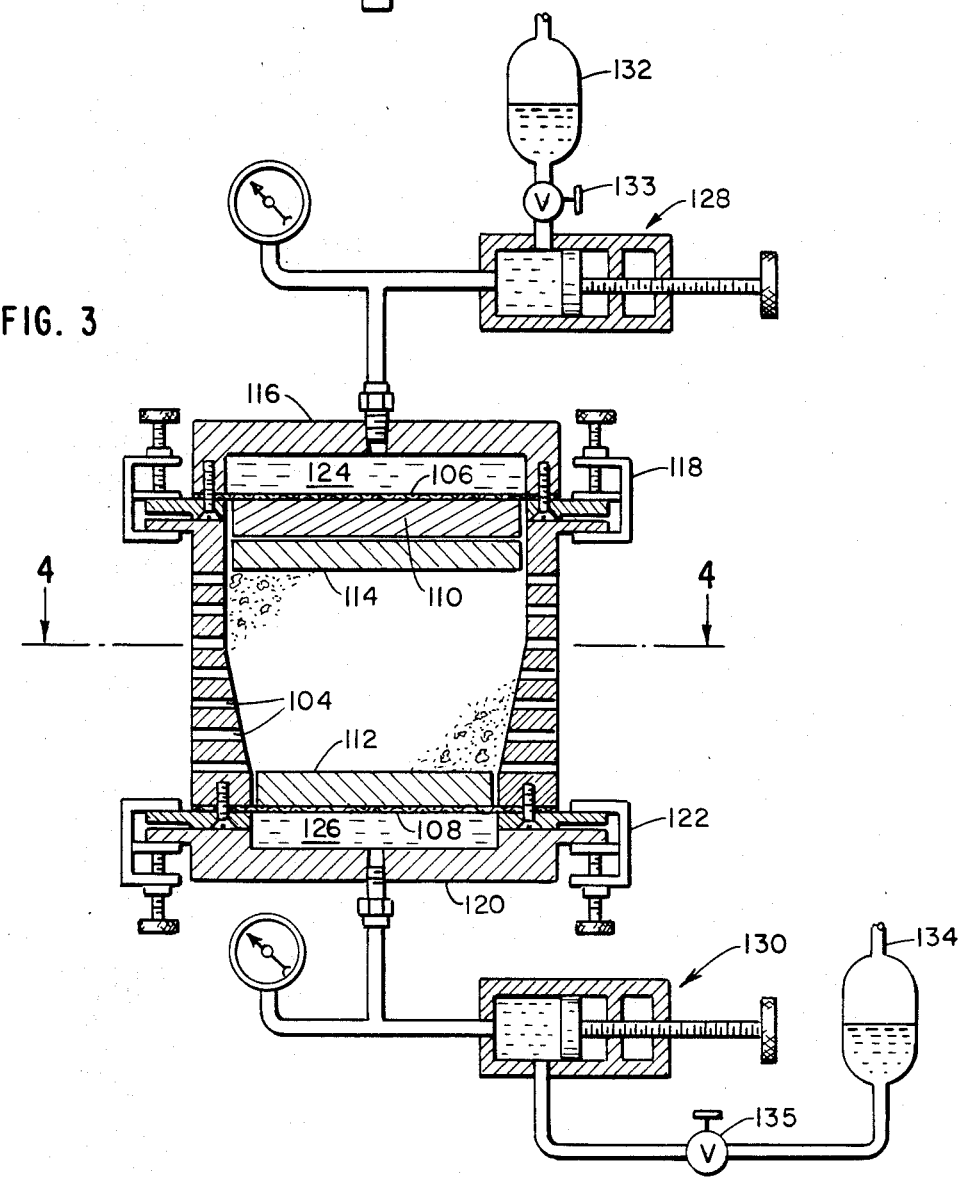
FIG. 3 is an elevation in section of a simplified embodiment of the test cell.

FIGS. 3 and 4 illustrate a simplified embodiment of the test cell that is not provided with the temperature controls or means for introducing a fluid. The cell comprises a body 102 with upper and lower cylindrical sections and a conical section as in FIG. 1, and with apertures 104 similar to the apertures 38 of FIG. 1. The upper end of the body 102 is covered by a flexible rubber or rubber-like diaphragm 106, and the lower end is covered by a similar diaphragm 108. A top plunger 110 is fastened to the diaphragm 106, and a bottom plunger 112 is fastened to the diaphragm 108. A spacer 114 of uniform thickness and similar in peripheral shape to the plunger 110 is provided for purposes hereinafter described.

A cover plate 116 is clamped to the body 102 by clamps 118. Similarly, a cover 120 is clamped to the body by clamps 122. The covers form diaphragm chambers 124 and 126 for applying pressure through liquid to the diaphragms. The pressure applying means, designated generally at 128 and 130 are similar to those applying pressure to the lower force rod 76 in FIG. 1, except that pressurized air supplies 132 and 134 are selectively connected through pressure regulating valves 133 and 135 to the liquid for maintaining a controlled pressure thereon as hereinafter described.

Figure 6:
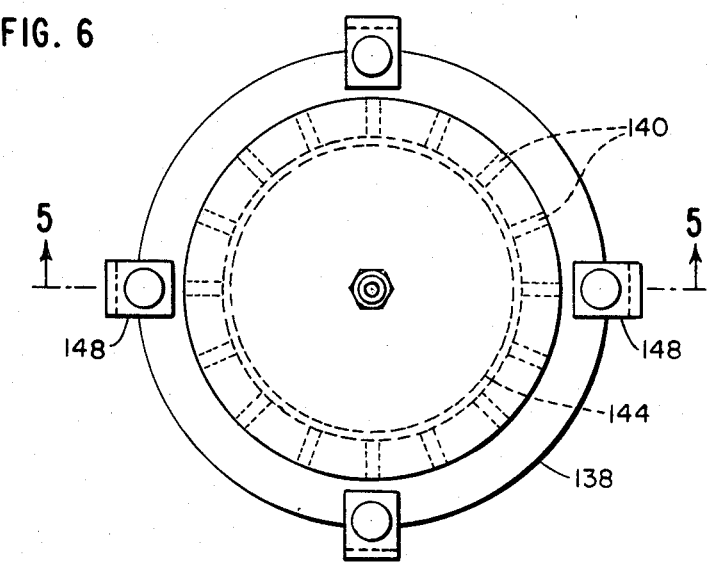
FIG. 6 is a plan view of the test cell of FIG. 5 with the manual pressure applying means removed.
Figure 5:
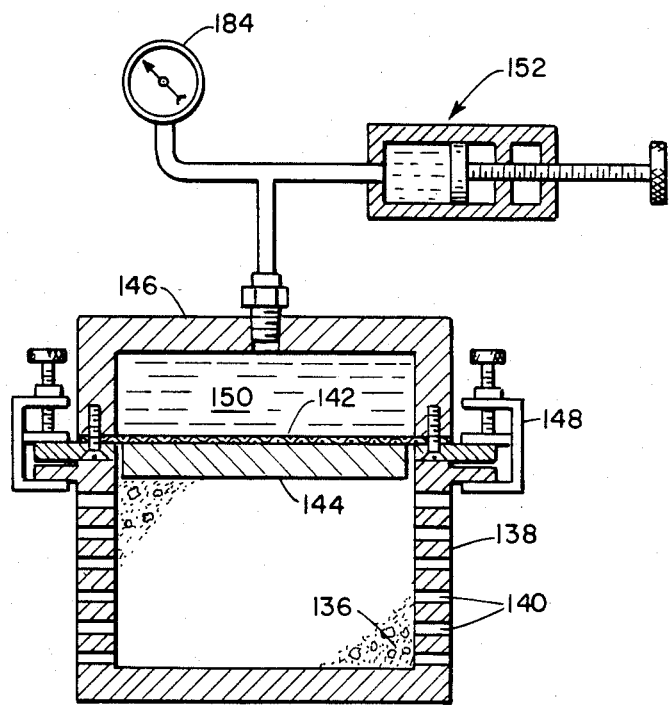
FIG. 5 is an elevation in section of a cylindrical test cell used to measure values of bulk density "D" employed in the calculations.

FIGS. 5 and 6 illustrate a variant of the above-described apparatus that can be used for measuring the bulk density of solids 136. A cylindrical body 138 having an array of apertures 140 similar to the apertures 38 and 104 has a closed bottom wall and is enclosed at the top by a diaphragm 142. A plunger 144 is fastened to the diaphragm and bears upon the solids 136. A cover 146 is secured to the body 138 by clamps 148. The cover encloses a body 150 of liquid to which pressure may be applied by manual pressure applying means 152 similar to the means 92-100 in FIG. 1.

Figure 8:
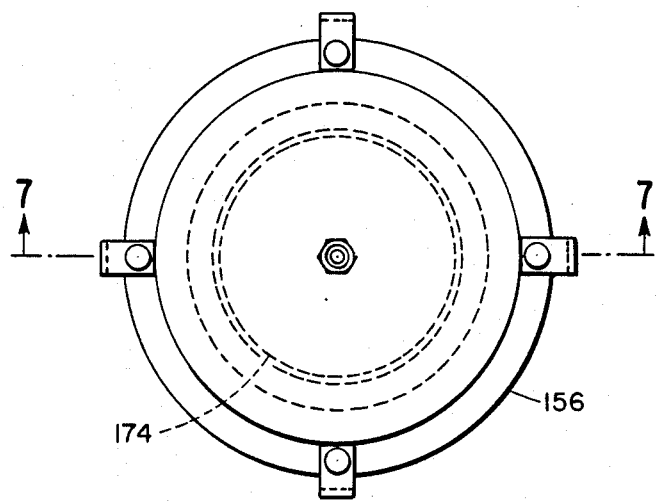
FIG. 8 is a plan view of the test cell of FIG. 7 with the pressure regulating valve and related parts removed.
Figure 7:
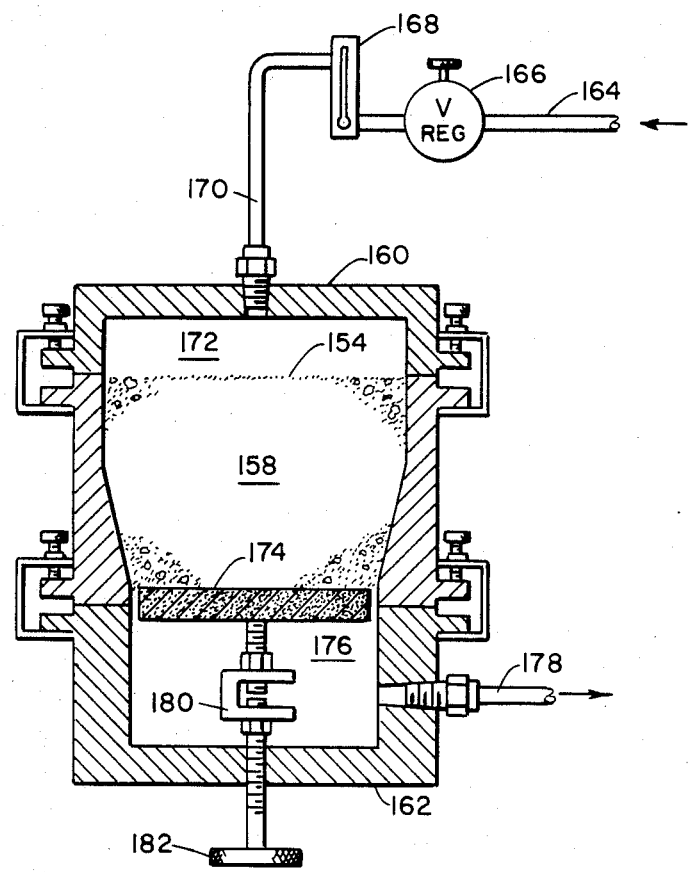
FIG. 7 is an elevation in section of a test cell adapted for applying gas pressure to the solids.

FIGS. 7 and 8 show a further variant of the test cell in which pressure is applied at the top cross section of bulk solids 154 under test by the direct application of gas pressure, instead of by a plunger. The cell comprises a body 156 defining upper and lower cylindrical sections and an intermediate conical section, similar in configuration to corresponding parts in FIGS. 1, 3 and 5, and the enclosure of the test chamber 158 is completed by cover plates 160 and 162. Gas pressure at an elevated level is connected with a pipe 164, the pressure being reduced by a regulating valve 166. The pressure is measured by a gauge 168 and connected by a pipe 170 to a space 172 above the solids 154.

At the lower end of the test chamber, a foraminous plunger 174 contacts substantially the entire lower cross sectional area of the solids 154. The plunger 174 may be formed in any desired manner, but in any case it is porous, permitting the flow of gas from the solids 154 to a space 176 vented at 178. A strain gauge 180 and threaded screw 182 provide means for both applying a measured force to the plunger 174.

In operation, a test for determining the effective angle of internal friction x and the unconfined yield strength $f_c$ in a body of bulk solids is next described in connection with FIGS. 1 and 2, the procedure for use with the embodiments of FIGS. 3 and 7 being the same. The test comprises two parts, the first part determining the valve of x and the second part determining the valve of $f_c$.

The first part of the test is initiated by loading a quantity of bulk solids 42 into the test chamber 40 and compacting the solids. The loading and compaction step consists in placing into the chamber successive layers of the solid, each having a thickness of about one-fourth of the diameter of the cell 14 at the top, compacting with the plungers 58 and 60 each layer as it is added to the cell. In view of the limited travel permitted by the bellows 64 (or the diaphragm of FIG. 3) one or more spacers like the spacer 114 in FIG. 3 are placed under the plunger 58. A preliminary decision is made as to the desired magnitude of the pressure within the solids at the initiation of the subsequent steps in the test, and force is applied by the applicator 72 until the force corresponding to this selected pressure is detected by the sensor 74. At the same time, sufficient pressure is applied to the bottom plunger 60 by turning the screw 100, so that only a slight downward motion of the force rod 76 is detected.

When the test cell has been loaded and compacted as described above, the next step in the test can be initiated. First, the force applicator 72 is operated to apply pressure to the top plunger 58 up to the above-mentioned predetermined value. At the same time the pressure on the lower plunger 60 is adjusted so that it will allow a slight downward motion of the rod 76. This will ensure that the solids are in a plastic state of stress. The pressures applied to the top and bottom plungers are recorded by observation of the sensor 74 and pressure gauge 96, respectively.

The pressure applied by the applicator 72 is then slightly increased and the resulting top and bottom plunger pressures are again recorded. When the ratio between the top and bottom pressures reaches a steady state value, the corresponding top and bottom pressures can be used in the next following step.

The next following step is to calculate a K-value which is defined as the ratio between the lateral and vertical stresses that were being applied to the solids at the end of the immediately preceding step. In general, this calculation necessitates the integration of the forces from the top to the bottom of the test cell, which is a function of its geometry. A simplified computation can be employed assuming that the change in the cross sectional area between the upper cylindrical section 16 and the lower cylindrical section 20 is negligible and that the height of the solids in the cylindrical section 16 is negligible. This leads to the following equation.

$$K = \frac{d\left[\frac{T-B}{h} + D\right]}{2(T+B)\tan F} \quad (1)$$

where:
d = average diameter of test cell
T = pressure applied by top plunger
B = pressure applied by bottom plunger
tan F = coefficient of friction between solids and wall of test cell (obtained by a conventional test)
D = bulk density of solids
h = height of material in test cell Following the computation of K the value of x can be found by consulting curves such as those shown in FIG. 9. These are a family of curves each corresponding to a particular value of x against coordinates of F and K. Curves of this type can be compiled by experimental methods already known in this art.

After the value of x has been determined, the value of $f_c$ is found by the following steps. First, pressure loads are applied to the top and bottom plungers and sustained for a sufficient length of time to simulate the period in which the solids may be held within material handling equipment. This is preferably done by means of an air supply and regulator valve as illustrated at 132 and 133 in FIG. 3. After the designated period of time the applied pressure is simultaneously removed from both the top and bottom plungers.

The bottom plunger 60 is then removed sufficiently so that it no longer contacts the bottom surface of the bulk solid 42. Then, the pressure applied by the force applicator 72 is increased until failure of the solids occurs at the bottom, as indicated by a sudden motion of the force rod 70. The peak pressure as indicated by the force sensor 74 is then recorded.

This peak pressure may then be used to calculate the unconfined yield strength $f_c$. In general, this calculation also requires an integration of forces from the top to the bottom of the test cell. However, assuming that the change in cross sectional area of the cell between the cylindrical sections 16 and 20 is negligible, a simplified form of calculation can be employed as follows.

$$f_c = \frac{b(D + T/h)}{2.2} \quad (2)$$

where: b = bottom diameter of test cell.

By this means a particular value of $f_c$ is found for each value of applied pressure. This part of the test is repeated several times using different compaction pressures to obtain the functional relationship between the unconfined yield strength and the compaction pressure.

It will be understood that during the tests described above, the conditions as to temperature and the flow of gas or liquid into and through the test chamber are suitably maintained to simulate the conditions to which the bulk solids are subjected in the handling apparatus. The testing steps employed with the embodiment of FIGS. 3 and 4, except for these additional provisions, are substantially the same as described above.

The embodiment of FIGS. 5 and 6 can be employed for determining the value of the bulk density D to be used in the foregoing calculations. A series of values of D are determined, each corresponding to a pressure value indicated by a gauge 184. The cell is loaded with a quantity of solids 136, after which the cell is closed and pressure is applied to the liquid 150. The pressure is elevated to a predetermined value and sustained to allow compaction of the solids. After the solids are compacted the cell is weighted, and from this weight the weight of the empty cell is subtracted. The volume occupied by the compacted solids is accurately measured. From this data the bulk density corresponding to the particular applied pressure is calculated. This is repeated for a number of values of applied pressure.

As stated above, the embodiment of FIGS. 7 and 8 may also be used to perform the tests for x and $f_c$, following substantially the same procedures described above. In this case, gas pressure in the space 172 is used both to consolidate the sample of bulk solid and to cause it to fail in the determination of unconfined yield strength. In order to obtain proper operation of this embodiment, it is necessary that the top of the test cell be closed to allow a buildup of gas pressure, and the bottom plunger 174 is of porous construction with the space 176 side vented to allow gas to be expelled. The gas pressure and resulting gas flow cause a pressure gradient across the material which compacts and pushes on it in a manner analogous to the action of the top plungers in FIGS. 1 and 3. The magnitude of the forces that can be applied with this embodiment is limited by the gas pressure gradient that can be attained, and therefore this embodiment is generally limited to the testing of bulk solids in the form of fine powders where the permeability is sufficiently low to allow for a significant pressure gradient to be attained. The test procedures and simplified calculations described above are applicable to this embodiment, with the gas pressure in the space 172 being the value of T in the equations.

I claim:

1. Testing apparatus for bulk solids comprising, in combination,
   a test cell for containing the solids having a laterally enclosing wall converging from a first end toward a second end thereof, the cross sectional area of the first end exceeding the cross sectional area of the second end,
   means for applying pressure to the solids over said area of the first end including means to increase said pressure and a sensor for measuring said pressure, and
   means extending over said area of the second end, movable in the direction toward and away from the first end and adapted to confine the solids in the cell.

2. Testing apparatus according to claim 1, in which the test cell has a vertical wall of conical shape.

3. Testing apparatus according to claim 1, in which the pressure applying means comprise a plunger.

4. Testing apparatus according to claim 1, including a sealed expansible chamber in force-applying engagement with the plunger and means for applying a measured variable fluid pressure to the chamber.

5. Testing apparatus according to claim 1, in which the test cell is ported for escape of gas from the pressurized solids.

6. Testing apparatus according to claim 5, in which said wall is foraminous.

7. Testing apparatus according to claim 1, in which said cell has a faraminous plunger.

8. Testing apparatus according to claim 6, including means to conduct a gas through a first portion of said wall into the cell and through a second portion of said wall from the cell.

9. Testing apparatus according to claim 1, including means for controlling the temperature of the test cell.

10. Testing apparatus according to claim 1, including pressure applying means adapted to apply fluid pressure directly to the surface of the solids over the cross sectional area at the first end.

11. Testing apparatus according to claim 1, in which the last-mentioned means comprise a plunger having means for applying a variable force thereto and a second sensor for measuring said force.

12. A method of testing the properties of bulk solids comprising the steps of
   confining a sample of said solids within a test cell having a laterally enclosing wall converging from one end toward the other whereby the cross sectional area of the sample is greater at said one end than at the other,
   applying an independently controlled and measured pressure to the sample at each said end,
   and increasing the pressure applied to said one end until the ratio thereof to the resulting pressure at the other end reaches a steady state value.

13. The method according to claim 12, in which gas is permitted to escape from the test cell during said application of pressure.

14. The method according to claim 12, including the step of passing a fluid into the test cell, through the sample and from the test cell during said application of pressure.

15. A method of testing the properties of bulk solids comprising the steps of
   confining a sample of said solids within a test cell having a laterally enclosing wall converging from one end toward the other whereby the cross sectional area of the sample is greater at said one said end than at the other,
   applying a measured pressure to said one end while confining the solids in the cell over the area of said second end,
   removing the applied pressure,
   removing the confinement of the solids over said last-mentioned area,
   reapplying and increasing a measured pressure to said one end until the solids fail at said other end, and
   detecting the value of the applied pressure when said failure occurs.

* * * * *